(12) United States Patent
Fleischer et al.

(10) Patent No.: US 8,373,205 B2
(45) Date of Patent: Feb. 12, 2013

(54) SIGNAL QUALITY OF FIELD EFFECT TRANSISTOR-BASED HUMIDITY SENSORS OR GAS SENSORS

(75) Inventors: Maximilian Fleischer, Hoehenkirchen (DE); Roland Pohle, Herdweg (DE); Oliver von Sicard, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 624 days.

(21) Appl. No.: 12/585,792

(22) Filed: Sep. 24, 2009

(65) Prior Publication Data

US 2010/0071460 A1  Mar. 25, 2010

(30) Foreign Application Priority Data

Sep. 24, 2008  (DE) .......................... 10 2008 048 715

(51) Int. Cl.
*G01N 27/403*  (2006.01)
*G01N 27/12*  (2006.01)
(52) U.S. Cl. ........................ 257/253; 73/31.06
(58) Field of Classification Search .................. 257/253; 73/31.05, 31.06
See application file for complete search history.

(56) References Cited

U.S. PATENT DOCUMENTS

| | | | |
|---|---|---|---|
| 4,158,807 A * | 6/1979 | Senturia ........................ 324/71.1 |
| 5,698,771 A | 12/1997 | Shields et al. |
| 2004/0133116 A1* | 7/2004 | Abraham-Fuchs et al. .. 600/532 |
| 2006/0270053 A1 | 11/2006 | Tilak et al. |
| 2008/0016949 A1 | 1/2008 | Fleischer et al. |
| 2010/0193375 A1 | 8/2010 | Liemersdorf et al. |

FOREIGN PATENT DOCUMENTS

| | | |
|---|---|---|
| DE | 44 44 827 | 6/1996 |
| DE | 198 14 857 | 10/1999 |
| DE | 198 49 932 | 5/2000 |
| DE | 199 56 744 | 6/2001 |
| DE | 10 2004 019 604 | 11/2005 |
| DE | 10 2007 029 153 | 8/2009 |
| EP | 1 191 332 | 3/2002 |
| WO | 99/51976 | 10/1999 |
| WO | 00/26656 | 5/2000 |

OTHER PUBLICATIONS

German Office Action for related German Patent Application No. 10 2008 048 715.5, mailed on Nov. 25, 2011.

* cited by examiner

*Primary Examiner* — Lisa Caputo
*Assistant Examiner* — Punam Roy
(74) *Attorney, Agent, or Firm* — Staas & Halsey LLP

(57) ABSTRACT

Humidity or a gas concentration or a solvent concentration in at least one gas is detected by a field effect transistor-based gas sensor whose sensor signal is generated by the change in the work function on a sensitive film. Detection is to be provided in a simple, effective and inexpensive manner. An additional change in potential is impressed at a gate of the field effect transistor and a variable of the resulting change in the sensor signal relative to the additional change in potential is evaluated. For example, each variable, which is e.g. a ratio, can be assigned a relative humidity, a gas concentration, or a solvent concentration. Sensitive films having at least one polymer are particularly advantageous.

20 Claims, 4 Drawing Sheets

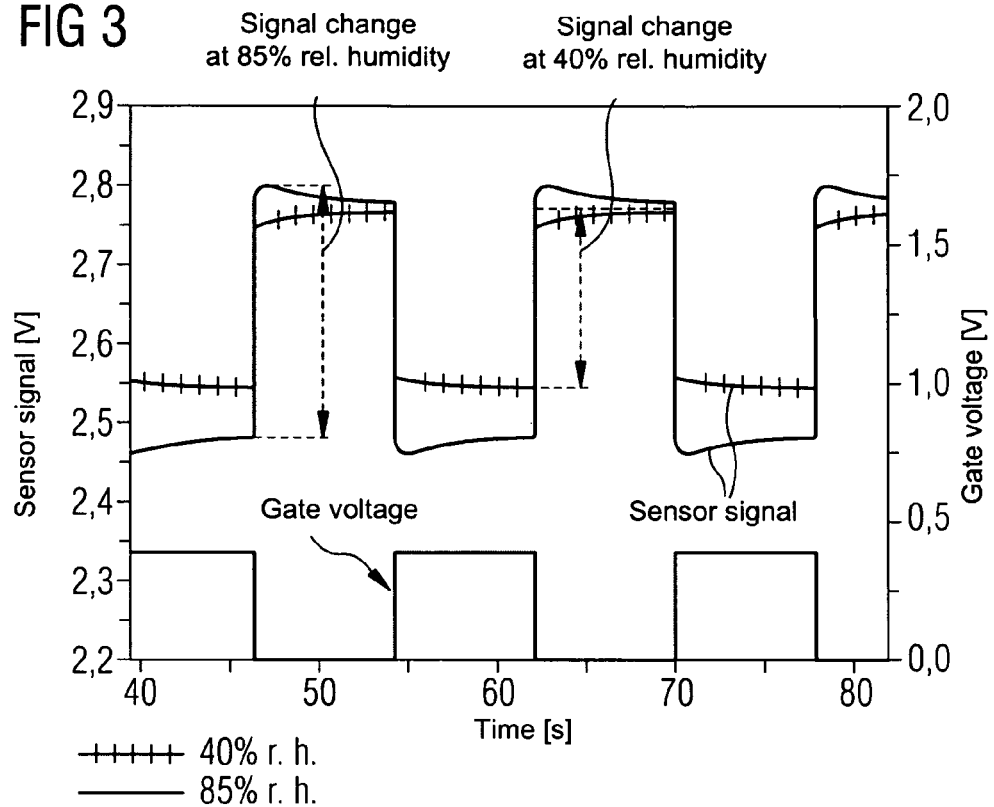
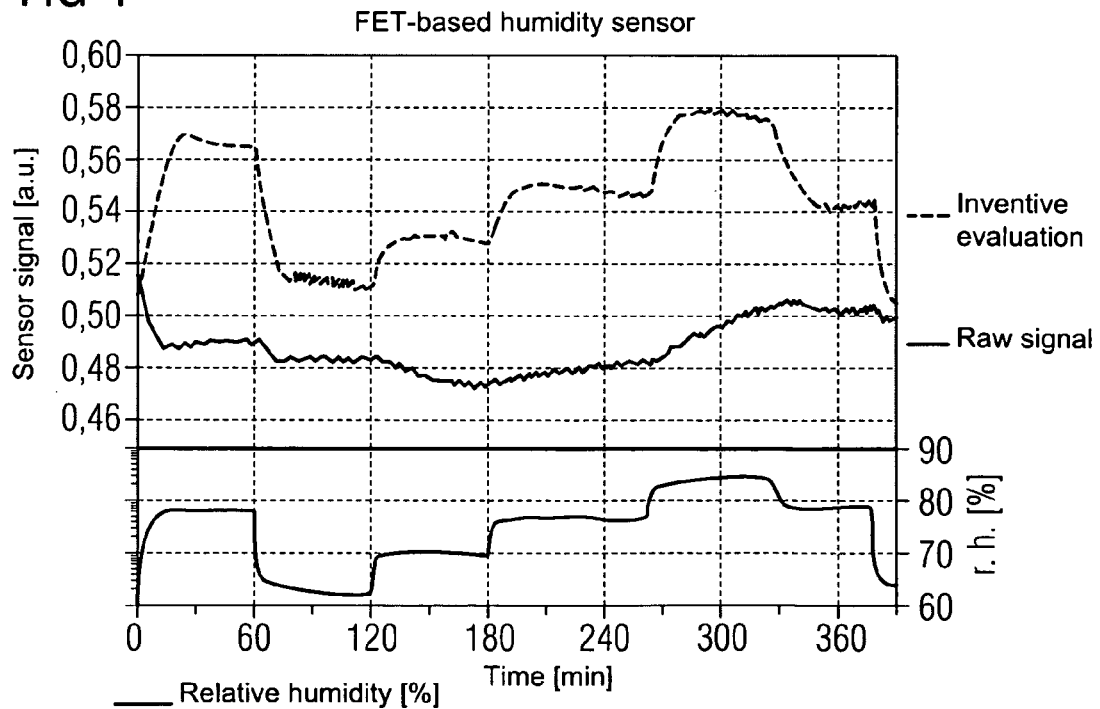

—— Sensor raw signal
······· Gate voltage

SIGNAL QUALITY OF FIELD EFFECT TRANSISTOR-BASED HUMIDITY SENSORS OR GAS SENSORS

CROSS REFERENCE TO RELATED APPLICATIONS

This application is based on and hereby claims priority to German Application No. 10 2008 048 715.5 filed on Sep. 24, 2008, the contents of which are hereby incorporated by reference.

BACKGROUND

Of particular interest is the precise detection of moisture in gas mixtures, such as air, for example, using a small and inexpensive structure.

Conventionally, the following five methods are basically used for humidity sensing:

a.) Capacitive humidity measurement. Here a hygroscopic polymer film is used whose dielectric constant is changed by water absorption corresponding to the relative humidity. The thus changed capacitance of the capacitor is directly proportional to the relative humidity.

b.) Psychrometric humidity measurement. Psychrometers are devices which are equipped with a wet temperature sensor and a dry temperature sensor. Evaporation causes the wet sensor to cool down. The humidity can be ascertained by determining the temperature difference between the two sensors.

c.) Hygrometric humidity measurement. Hygrometric transducers are equipped with a material which expands or contracts depending on the humidity. Organic materials, plastics or porously sintered ceramic materials such as aluminum oxide or zinc oxide are used.

d.) Chilled mirror dewpoint hygrometer. With this very precise measuring method, the condensation of water vapor is evaluated by dewpoint discrimination. The temperature of a mirrored surface is reduced until it just begins to fog. The temperature measured at this moment corresponds to the dewpoint temperature.

e.) Laser-based humidity measurement. Laser-based humidity measurement uses the characteristic optical absorption of water vapor in the infrared region of the spectrum. Because of the optical path length required, this likewise very accurate method is of a size which is disadvantageous for many applications.

The disadvantage of conventional measurement systems of this kind is that they are either cost-intensive, e.g. as a result of a chilled mirror or laser optics, or do not achieve the required measuring accuracy for many applications.

Through the use of standard processes for producing semiconductor components (CMOS), conventional gas sensors based on suspended gate field effect transistors (SGFETs) have the potential to be very inexpensive to manufacture. CMOS stands for complementary metal oxide semiconductor. In addition, a sensor of this kind requires minimal electrical energy for its operation. The construction and method of operation are known e.g. from DE 19814857, DE 19956744 and DE 19849932. A large number of materials can be used for sensitive films of such gas sensors, making this technology a platform for manufacturing a large number of different gas sensors. For humidity measurement, e.g. polymers are used as the sensitive material, as disclosed in EP 1191332. The construction of an SGFET is shown schematically in cross-section in FIG. 1. Over the field effect transistor comprising a source electrode S and a drain electrode D, a gas sensitive film is disposed above an air gap. By absorption of the gas on a sensitive film, an initial change in potential is brought about which in turn causes the current through the transistor to change. Such a change in the current represents the sensor signal. Such a change in potential constitutes a first change in potential.

Conventional semiconductor devices are protected from environmental effects by hermetic sealing, e.g. by potting compounds. In the case of the gas sensors described here, by virtue of their operating principle, the part of the chip surface which together with the actual sensitive material constitutes the gas-sensitive part of the structure cannot be protected in this way. Due to the effect of environmental influences such as humidity and temperature, this unprotected surface is subject to processes resulting in undesirable instabilities in the sensor signal such as baseline drift or diminution of the gas signal. Another major difficulty is the requirement for selective detection of a gas component, i.e. in general the sensor signal is affected not only by the gas component to be detected but also by other gases. To reduce signal drift in GasFETs, the following approaches have been adopted.

The operating temperature is increased. By increasing the operating temperature, the unwanted effect of humidity and temperature can be reduced by stabilizing the operating temperature. Disadvantageously, due to the heating power necessary, the power consumption of the sensor is increased such that the advantage of low energy requirement is lost. For humidity sensors, an additional effect produced is that the relative humidity at the sensor reduces while the ambient humidity remains constant, which diminishes the measuring effect.

DE 10 2004 019 604 discloses an operating method for a GasFET which evaluates both the work function and the change in the capacitance of the sensitive film. This is used to improve the sensitivity of the gas sensor, specifically to reduce the sensitivity to humidity.

SUMMARY

One potential object is to provide a method and a device for simple, effective and inexpensive detection of moisture, a gas concentration or a solvent concentration in a gas.

The term solvent is taken to mean a substance which can dissolve gases, other liquids or solids without chemical reactions occurring between dissolved substance and dissolving substance. Although in general liquids are used for dissolving other substances, solids can also dissolve other substances.

The concentration of a pure substance (of the solute) in a mixture with a solvent is an important variable in the natural sciences, particularly chemistry. Concentration is a measure of how much of the substance is present in a reference quantity of the overall mixture, i.e. of solvent and solute. Solute and solvent can also be identical.

The inventors propose a method for measuring a humidity or a gas concentration or a solvent concentration in at least one gas by a field effect transistor-based gas sensor whose sensor signal is generated by the change in the work function on a sensitive film. The change in the work function is brought about by a change in the humidity or gas concentration or solvent concentration such that a first change in potential on the sensitive film is produced. According to the first aspect, a change in potential additional to the first change in potential is impressed at a gate of the field effect transistor and a variable is evaluated from the resulting change in the sensor signal relative to the additional change in potential. For example, the ratio of the resulting change in the sensor signal to the additional change in potential can also be evaluated as this variable. An evaluation can likewise take place on the basis of a difference between the change in the sensor signal and the additional change in potential. Other evaluations or variables are likewise possible.

An additionally impressed change in potential at the gate of the FET-based gas sensor means a further influencing of the gate voltage, here supplementing the first influencing of the gate voltage by the change in the work function on the sensitive film due to a change in the value of a humidity, gas concentration or solvent concentration to be detected. Impressing a change in potential means applying a changing voltage.

The ratio of the change in the sensor signal to the additionally impressed change in potential at the gate corresponds to the slope of the characteristic of the field effect transistor. On the basis of changing ratios, a change in the slope of the transistor characteristic can likewise be measured. For the ratio, the resulting change in the sensor signal is in the numerator and the additional change in potential in the denominator.

Each variable from the resulting change in the sensor signal relative to the additional change in potential can be assigned a humidity or a gas concentration or a solvent concentration. On this basis a sensor characteristic can be provided.

The proposed method differs from DE 10 2004 019 604 in that it is not a capacitance that is measured, but the change in the slope of the transistor characteristic which can be measured, i.e. the gradient in the linear region as shown in FIG. 2.

By variation of the voltage applied to the gate electrode of the sensor, a change in the output signal of the sensor, i.e. in the sensor signal, is induced. The ratio of the change in the sensor signal to the change in potential at the gate electrode is termed transconductance. This parameter is dominated by volume effects in the sensitive film and is therefore much less affected by unwanted interference effects such as surface conductivity on the chip, in contrast to the original output signal or rather sensor signal.

With the proposed operating method, the signal quality of gas-sensitive field effect transistors can be significantly improved so that, for the first time, a signal quality comparable to commercially available reference sensors can be achieved with a GasFET.

By using the sensor technology described, it is possible for a high-quality relative humidity sensor to be incorporated with other gas sensors based on the same technology.

According to a second aspect, the material of the sensitive film has at least one polymer. With suitable sensor materials, the transconductance has a marked sensitivity to changes in relative humidity and is used as a stable measured variable. A group of sensor materials to which this method can be particularly well applied are the polymers. They are used as sensitive materials for detecting humidity or solvents. When these substances are detected by the polymer, they dissolve in the polymer. This brings about on the one hand, for example, an increase in the relative dielectric constant of the polymer sensor film and, on the other, also a macroscopic volume change, i.e. an increase in the film thickness. Both result in improved coupling of the gate potential to the FET channel, thereby changing the transconductance of the GasFET. In other words, materials such as polymers constitute suitable sensor materials.

According to an advantageous embodiment, the sensor signal is a source-drain current of the field effect transistor. This is a simple case of a sensor output signal. Alternatively, the sensor signal is a voltage produced across an electrical resistance by the source-drain current.

According to another advantageous embodiment, the additionally impressed change in potential is implemented with a time constant in the range from 1 ms-100 ms. The transconductance of the transistor is measured using a very small time constant. The gate voltage is typically varied with time constants ranging from 1 ms to 100 ms. During this very short time, any undesirable surface conductivities occurring produce many fewer changes in the measured value than during typical gas sensor response times of seconds or minutes, or to an even greater extent during the times in which, in the use of ambient air monitoring, a stable zero point is expected from gas sensors, these periods ranging from days to years.

According to another advantageous embodiment, the additionally impressed change in potential is repeated by applying voltage pulses, the time constants for varying the voltage being provided in the range 0.1 ms to 1000 ms. The transconductance can be determined by applying rapid voltage pulses, the typical time constants for varying the voltage here being in the range 0.1 ms to 1000 ms. To increase the signal-to-noise ratio, only the change in the source-drain current in this range is evaluated.

According to another advantageous embodiment, the additionally impressed change in potential is repeated by applying a sinusoidal voltage, the frequency being generated in the range from 1-1000 Hz. The sinusoidal change in gate potential constitutes a metrologically very interesting variant. The frequencies can be in the 1-1000 Hz range, producing a sinusoidal waveform of the source-drain current, for example.

According to another advantageous embodiment, a spectral component of the source-drain current is read out by a lock-in process. Through the use of a read-out in accordance with lock-in technology, only the corresponding spectral component of the source-drain current can then be read out, thereby achieving particularly good suppression of drift phenomena.

According to another advantageous embodiment, the shape of a sensor characteristic is optimized by selecting the point in time at which the sensor signal is read out at or after the additionally impressed change in potential. A sensor characteristic shows, for example, a percentage relative humidity as a function of the ratio of the resulting change in the sensor signal to the additional change in potential. A sensor characteristic is optimum, for example, if the entire range e.g. of a relative humidity is detected or if the sensor characteristic exhibits a slight gradient.

According to another advantageous embodiment, the sensor signal is read out at a plurality of points in time at and after the additionally impressed change in potential at the gate, the read-out values generated being combined by an unambiguous mathematical operation to improve the measuring accuracy of the sensor. To improve it still further, measured values can therefore also be recorded and evaluated at a plurality of times at and after a change in the gate voltage.

According to another advantageous embodiment, the mathematical operations are a linear combination or fractional rational functions. Any other unambiguous mathematical operation can likewise be used to improve the measuring accuracy of the sensor.

According to another advantageous embodiment, the polymer is polyamide or a polysiloxane. Particularly advantageous is the use of polyamide for humidity detection or of polymers from the polysiloxane group, such as heteropolysiloxane, for example, which are suitable for detecting a large group of gases. Polymers can be used which on the one hand detect polar gases, or polymers which exhibit a particularly marked tendency for the material to swell up on detection of the gas.

According to another advantageous embodiment, the sensitive film material has at least one porous, or finely porous oxide. Other sensor materials suitable for implementing the proposed method are therefore, for example, porous or finely porous oxides. Here, e.g. atmospheric humidity reversibly accumulates in the pores of the material and causes a change in the relative dielectric constant. In this case no swelling of the material occurs.

According to another advantageous embodiment, the material of the sensitive film contains at least one zeolite, i.e. other suitable materials are zeolites. These have compartments in the nanometer range in which gas molecules can be reversibly stored, where these again produce a change in the dielectric constant and no swelling of the material.

According to another advantageous embodiment, the field effect transistor is an SGFET or a CCFET.

A CCFET (Capacitively Controlled Field Effect Transistor) is a field effect transistor in which a capacitance is formed by a gas-sensitive film and an air gap, and an electrical potential is transferred to a separately mounted read-out field effect transistor via an electrically conductive connection. DE 43 33 875 A1 discloses an example of a CCFET. An SGFET (Suspended Gate Field Effect Transistor) is a gas-sensitive gated field effect transistor with an air gap between a passivated channel produced between a drain and a source and a film of sensor material which is a component part of the gate. One use of an SGFET is adsorption of molecules of a gas to be detected on the surface of the sensor material accompanied by production of a dipole layer and an electrical potential which influences via the air gap the channel conductivity and therefore a source-drain current which flows through an electrical resistance, thereby generating a voltage, the change in which is the sensor signal. The sensor signal can likewise be directly constituted by the change in the source-drain current.

According to another advantageous embodiment, a voltage source, in particular a sine-wave generator, provides the additionally impressed change in potential at the gate.

According to another advantageous embodiment, a computer device calculates a variable from the sensor signal and the additionally impressed change in potential. The variable can be a ratio, for example.

According to another embodiment, a lock-in amplifier reads out a spectral component of the source-drain current. A lock-in amplifier is an amplifier for measuring a weak electrical signal which is modulated with a reference signal of known frequency and phase. The device constitutes an extremely narrowband bandpass filter, thereby improving the signal-to-noise ratio. The advantage is that DC voltages, AC voltages of another frequency and noise can be efficiently filtered.

According to another advantageous embodiment, a display device such as a monitor displays a sensor characteristic.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 3 shows the sensor signal and gate voltage waveforms;

FIG. 4 shows a conventional sensor signal and a sensor signal according to the proposed method;

DETAILED DESCRIPTION OF THE PREFERRED EMBODIMENT

Figure 1:
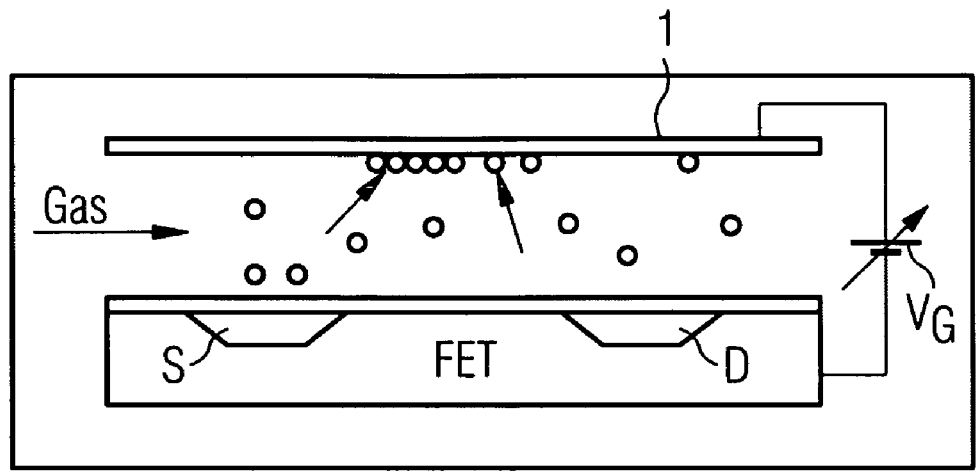
FIG. 1 shows an exemplary embodiment of a conventional SGFET.

Reference will now be made in detail to the preferred embodiments of the present invention, examples of which are illustrated in the accompanying drawings, wherein like reference numerals refer to like elements throughout.

FIG. 1 shows an exemplary embodiment of a conventional SGFET. The structure of the SGFET is shown schematically in cross-section. Above the field effect transistor indicated by a source electrode S and a drain electrode D, the gas-sensitive film 1 is disposed above an air gap. Due to absorption of the gas on the sensitive film, a first change in potential is produced which in turn brings about a first change in the current through the transistor. This current change constitutes the sensor signal.

Figure 2:
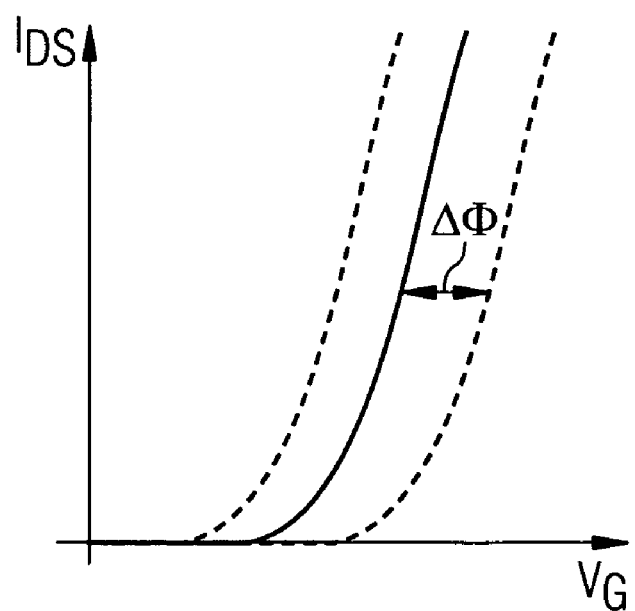
FIG. 2 shows transistor characteristics of an FET.

FIG. 2 shows transistor characteristics of an FET (field effect transistor) wherein the position of the transistor characteristic changes due to the change in the work function of the sensitive film. $\Delta\phi$ represents the change in the work function which brings about a first change in the gate potential. An additional gate potential change is a second change in the gate potential.

FIG. 3 shows the waveform of the sensor signal as a function of the gate voltage according to the method. The gate voltage changes e.g. by 0.4 V every 8 seconds. The impressing of an additional change in potential is effected by applying a square-wave voltage of this kind to the gate of the FET. When the gate voltage rises or falls, a change in the sensor signal as a function of the relative humidity is induced. As shown in FIG. 3, the change in the sensor signal is larger, the greater the relative humidity. FIG. 3 illustrates how the transconductance can be determined by varying the gate voltage. The change in the output signal of the sensor is normalized to the change in the gate potential to determine the transconductance. A sensor signal change for 85% relative humidity has a value of e.g. 0.3 V.

FIG. 4 shows a comparison of the output signal of an FET sensor for conventional humidity measurement to the signal obtained by the method. The signal obtained by the method reflects the change in the relative humidity much better than the unprocessed output signal of the FET sensor. According to the method, each relative humidity is assigned a variable from the resulting change in the sensor signal and the additional changes in potential. This variable can be a ratio, for example.

Figure 5:
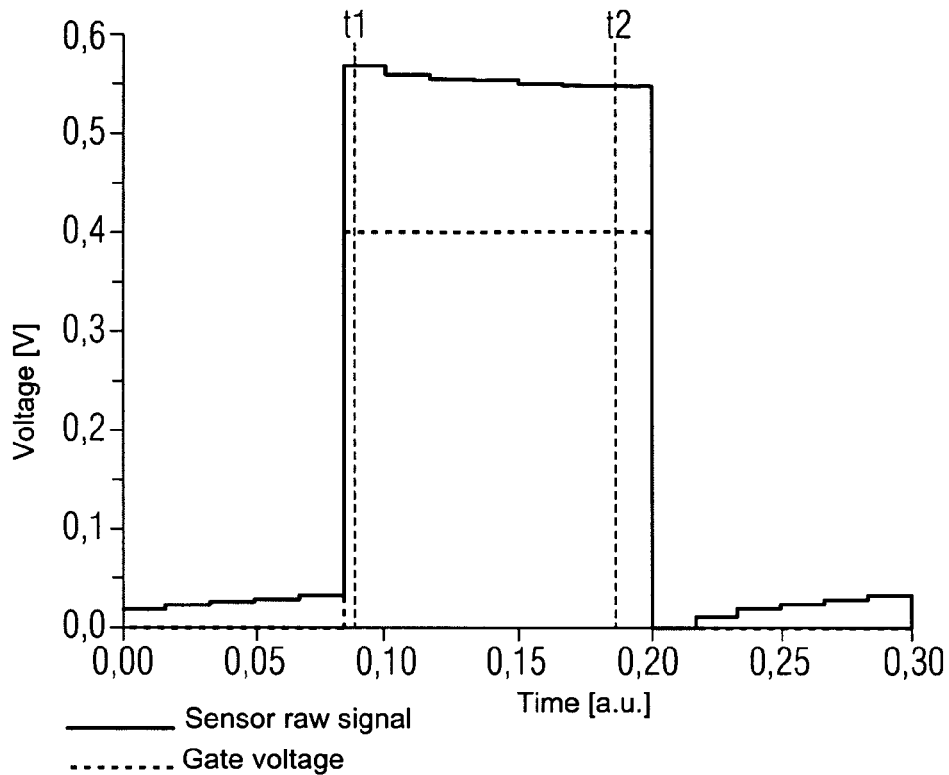
FIG. 5 shows the variation of the evaluation instant for applying the gate voltage.

FIG. 5 shows a variation of the measuring instant of the change in the sensor signal. The value of the signal change as a result of the additional change in potential can be determined at different evaluation instants. By varying the point in time, e.g. the times t1 and t2 in FIG. 5, at which the signal is evaluated after a change in the gate voltage, the shape of the sensor characteristic can be improved further. This is illustrated in FIG. 6.

Figure 6:
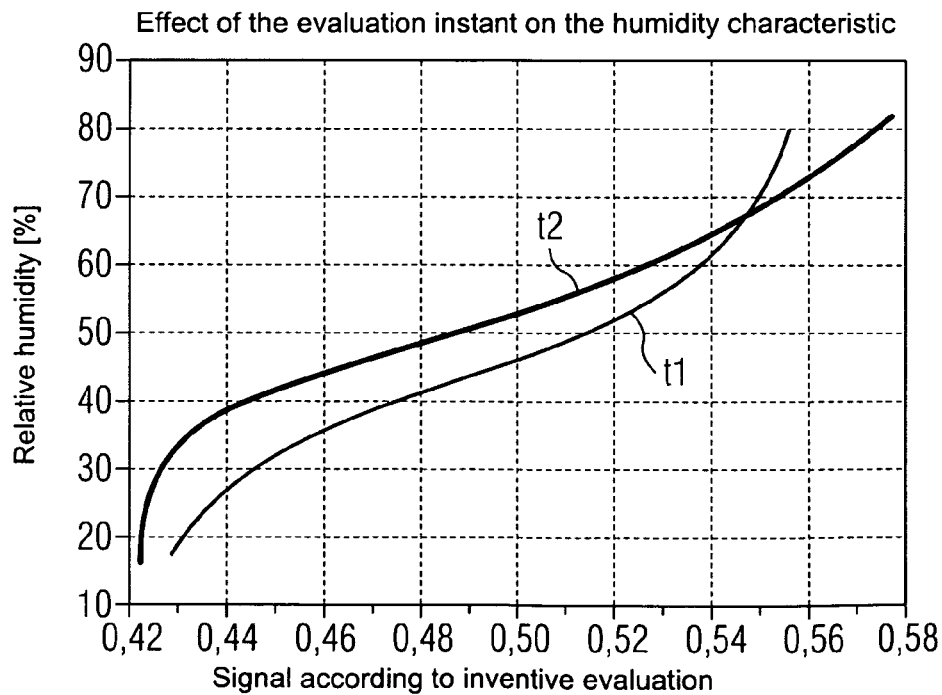
FIG. 6 shows humidity characteristics according to different evaluation instants.

FIG. 6 shows the effect of the evaluation instant on the humidity characteristic or rather sensor characteristic. By varying the point in time at which the signal is evaluated after a change in the gate voltage, the shape of the sensor characteristic can be improved further. A sensor characteristic is advantageous if a large relative humidity range can be detected. In addition, the sensor characteristic must not be too steep, as otherwise a small change in the size of the resulting change in the sensor signal relative to the additional change in potential means a large change in the relative humidity, so that large measuring errors could be produced.

FIG. 5 shows the variation in the evaluation point when the gate voltage is applied. FIG. 6 shows a comparison of the humidity characteristic obtained with the method for different evaluation instants.

Figure 7:
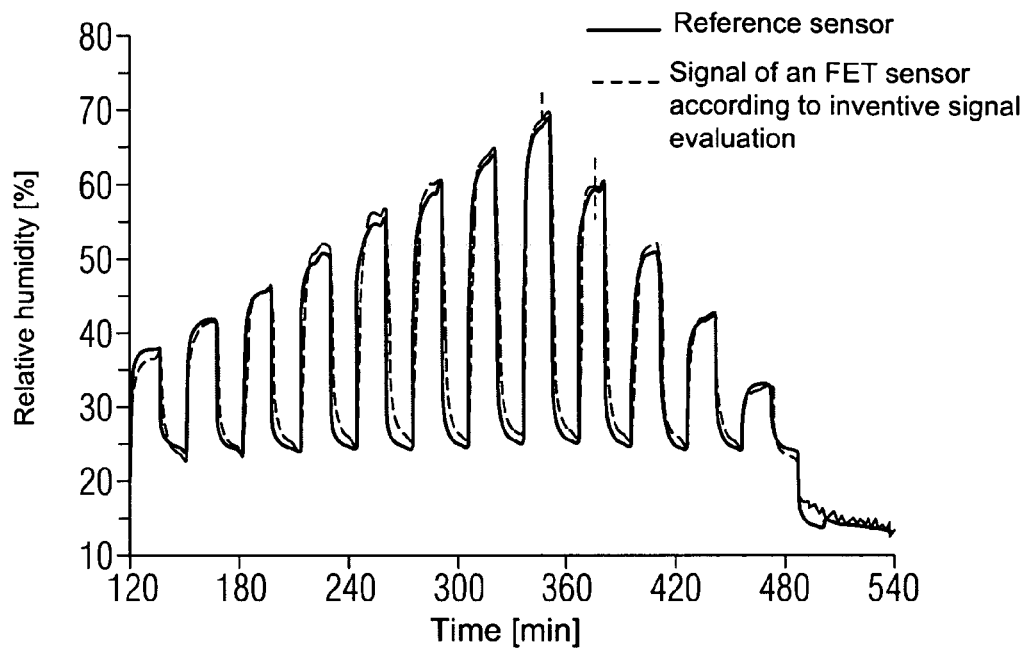
FIG. 7 shows the output signals of a humidity measurement according to the proposed method compared to a reference sensor.

FIG. 7 shows a comparison of the signal of an FET sensor for humidity measurement, with the signal of a reference sensor. It can be seen that the relative humidity is very accurate. The deviations of the signals of reference sensor relative to the sensor signal are very small.

Figure 8:
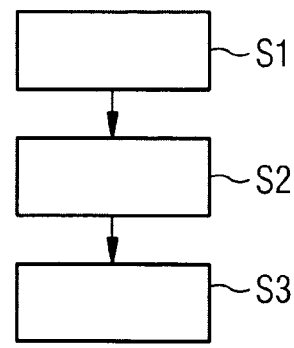
FIG. 8 shows the procedural steps of the proposed method.

FIG. 8 shows an exemplary embodiment of a method. With a step S1, an additional change in potential U is impressed at the gate of a field effect transistor. With a step S2, a variable is calculated from the resulting change in the sensor signal as a result of the additional change in potential, and the additional change in potential U. With a step S3, a variable can be assigned an unambiguous relative humidity using an already determined sensor characteristic. Instead of the relative humidity, a gas concentration or a solvent concentration can likewise be assigned.

Figure 9:
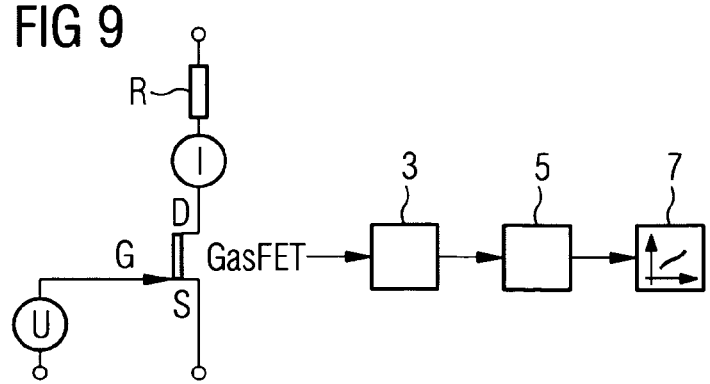
FIG. 9 shows an exemplary embodiment of a proposed device.

FIG. 9 shows an exemplary embodiment of a device. It shows a GasFET with a source S, a drain D and a gate G. A changing voltage U is applied to the gate G. Applying the additional change in potential produces a change in the sensor signal which can be e.g. the source-drain current I. The current I can be converted in an electrical resistance R to a voltage I*R. The additionally impressed change in potential can be provided e.g. by a voltage source, in particular a sign-wave generator. When using an alternating voltage U of this kind, a lock-in amplifier 3 is used which reads out a spectral component of the source-drain current I. From the variable provided by the lock-in amplifier 3, a computer device 5 calculates e.g. the ratio or other variables from the sensor signal and the additionally impressed change in potential U. A display device 7 displays a sensor characteristic. Correspondingly, each variable from the resulting change in the sensor signal relative to the additional change in potential, e.g. each ratio, can be assigned a value of a relative humidity or of a gas concentration or of a solvent concentration.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

What is claimed is:

1. A method for detecting a humidity or a target gas concentration or a solvent concentration in an ambient gas, comprising:
generating a sensor signal from a field effect transistor-based gas sensor having a gate on a sensitive film, the sensor signal being generated by a change in work function of the sensitive film;
applying changing potential to the gate of the field effect transistor; and
evaluating how the sensor signal changes relative to the changing potential applied to the gate, wherein
the shape of a sensor characteristic curve is optimized by adjusting a time between applying the changing potential and reading the sensor signal.

2. The method as claimed in claim 1, wherein
the sensor signal is a source-drain current of the field effect transistor or a voltage produced by the source-drain current at an electrical resistance.

3. The method as claimed in claim 1, wherein
the changing potential is applied to the gate with a time constant in a range 1 ms to 100 ms.

4. The method as claimed in claim 1, wherein
the changing potential applied to the gate is implemented by repeatedly applying voltage pulses, such that the voltage varies with time constants in a range 0.1 ms to 1000 ms.

5. The method as claimed in claim 4, wherein
the sensor signal is a source-drain current of the field effect transistor, and
a spectral component of the source-drain current is read out by a lock-in process.

6. The method as claimed in claim 1, wherein
the changing potential applied to the gate is implemented by applying a sinusoidal voltage having a frequency in a range 1 to 1000 Hz.

7. The method as claimed in claim 1, wherein
the sensor signal is read out at a plurality of instants, at and after the changing potential is applied to the gate,
each reading produces a measured value, and
the measured values are combined by a mathematical operation to improve the measuring accuracy of the sensor.

8. The method as claimed in claim 7, wherein
the mathematical operation is a linear combination or fractional rational functions.

9. A gas sensor device to detect a humidity or a target gas concentration or a solvent concentration in an ambient gas, comprising:
a field effect transistor having a source, a drain and a gate, the gate being associated with a polymer sensitive film separated from the source and the drain with a gap for the ambient gas, the field effect transistor generating a sensor signal from a change in work function of the sensitive film;
a voltage generator to apply a changing potential to the gate of the field effect transistor; and
an evaluation device to evaluate how the sensor signal changes relative to the changing potential applied to the gate, wherein
a computer device calculates a reference variable from the sensor signal and the changing potential applied to the gate, and
a display device displays a sensor characteristic curve.

10. The device as claimed in claim 9, wherein
the polymer is polyamide or a polysiloxane.

11. The device for carrying out a method as claimed in claim 9, wherein
the sensitive film contains a porous oxide or a zeolite.

12. The device as claimed in claim 9, wherein
the field effect transistor is a Suspended Gate Field Effect Transistor (SGFET) or a Capacitively Controlled Field Effect Transistor (CCFET).

13. The device as claimed in claim 9, wherein
the changing potential applied to the gate is generated by a sine-wave voltage generator.

14. The device as claimed in claim 9, wherein
the sensor signal is a source-drain current of the field effect transistor, and
a lock-in amplifier reads out a spectral component of the source-drain current.

15. A method for detecting a humidity or a target gas concentration or a solvent concentration in an ambient gas, comprising:
generating a sensor signal from a field effect transistor-based gas sensor having a gate on a sensitive film, the sensor signal being generated by a change in work function of the sensitive film;
applying changing potential to the gate of the field effect transistor; and
evaluating how the sensor signal changes relative to the changing potential applied to the gate, wherein
the sensor signal is a source-drain current of the field effect transistor or a voltage produced by the source-drain current at an electrical resistance.

16. The method as claimed in claim 15, wherein
the changing potential is applied to the gate with a time constant in a range 1 ms to 100 ms.

17. The method as claimed in claim 15, wherein
the changing potential applied to the gate is implemented by repeatedly applying voltage pulses, such that the voltage varies with time constants in a range 0.1 ms to 1000 ms.

18. The method as claimed in claim 15, wherein
the changing potential applied to the gate is implemented by applying a sinusoidal voltage having a frequency in a range 1 to 1000 Hz.

19. The method as claimed in claim 18, wherein
the sensor signal is a source-drain current of the field effect transistor, and
a spectral component of the source-drain current is read out by a lock-in process.

20. The method as claimed in claim 15, wherein
the sensor signal is read out at a plurality of instants, at and after the changing potential is applied to the gate,
each reading produces a measured value, and
the measured values are combined by a mathematical operation to improve the measuring accuracy of the sensor.

* * * * *